United States Patent
Phipps

(10) Patent No.: US 7,204,153 B2
(45) Date of Patent: Apr. 17, 2007

(54) APPARATUS AND A METHOD FOR TESTING ATTACHMENT FEATURES OF COMPONENTS

(75) Inventor: Anthony B Phipps, Uttoxeter (GB)

(73) Assignee: Rolls-Royce plc, London (GB)

( * ) Notice: Subject to any disclaimer, the term of this patent is extended or adjusted under 35 U.S.C. 154(b) by 114 days.

(21) Appl. No.: 11/122,111

(22) Filed: May 5, 2005

(65) Prior Publication Data

US 2005/0268728 A1 Dec. 8, 2005

(30) Foreign Application Priority Data

Jun. 5, 2004 (GB) ................................ 0412591.0

(51) Int. Cl.
*G01N 3/32* (2006.01)
(52) U.S. Cl. ............................ 73/808; 73/794; 73/804; 73/810; 73/813; 73/815; 73/821; 73/826; 73/845; 73/865.9
(58) Field of Classification Search .................. 73/794, 73/804, 808, 810, 811, 813, 815, 821, 826, 73/845, 865.9
See application file for complete search history.

(56) References Cited

U.S. PATENT DOCUMENTS

| | | | |
|---|---|---|---|
| 2,293,084 A | | 8/1942 | Sedam |
| 3,593,574 A | | 7/1971 | Omholt |
| 3,690,162 A | * | 9/1972 | Stecher ...................... 73/119 R |
| 3,802,255 A | | 4/1974 | Struthers et al. |
| 4,478,086 A | * | 10/1984 | Gram ........................... 73/781 |
| D287,932 S | * | 1/1987 | Seward et al. ............... D9/708 |
| 5,388,464 A | * | 2/1995 | Maddison .................... 73/856 |
| 5,863,183 A | * | 1/1999 | Dierksmeier et al. ... 416/241 R |
| 5,952,581 A | * | 9/1999 | Lammers et al. ............. 73/831 |
| 6,023,980 A | * | 2/2000 | Owen et al. ................... 73/797 |
| 6,250,166 B1 | | 6/2001 | Dingwell et al. |
| 6,601,456 B1 | * | 8/2003 | Davidson et al. ............. 73/808 |
| 6,718,833 B2 | * | 4/2004 | Xie et al. ...................... 73/812 |

(Continued)

FOREIGN PATENT DOCUMENTS

EP 0 267 492 A1 5/1988

(Continued)

*Primary Examiner*—Edward Lefkowitz
*Assistant Examiner*—Freddie Kirkland, III
(74) *Attorney, Agent, or Firm*—Oliff & Berridge, PLC

(57) ABSTRACT

An apparatus (10) for testing attachment features (26,28,30, 32) of components (12,14) comprises a first member (16) having a first end (18), a second end (20), a first edge (22) and a second edge (24). The first edge (22) has a first firtree slot (26) to receive a first component (12) and the second edge (24) has a second firtree slot (28) to receive a second component (14). The first component (12) has a firtree attachment feature (30) to fit the first slot (26) and the second component (14) has a firtree attachment feature (32) to fit the second slot (28). The first end (18) of the first member (16) has flanges (34,36) extending laterally and the second end (20) of the first member (16) has flanges (38,40) extending laterally such that the first member (16) is substantially H-shaped in cross-section. First load means (42) apply a load on the first component (12) and second load means (44) apply a load on the second component (14) substantially in the opposite direction to the load on the first component (12). The apparatus may be used to test firtree attachments for turbine blades and discs.

30 Claims, 4 Drawing Sheets

U.S. PATENT DOCUMENTS

| | | | |
|---|---|---|---|
| 6,732,591 B2 * | 5/2004 | Miles et al. | 73/808 |
| 6,813,960 B1 * | 11/2004 | Owen et al. | 73/808 |
| 6,848,311 B1 * | 2/2005 | Hull | 73/579 |
| 7,007,382 B2 * | 3/2006 | Mantel | 29/889.2 |
| 7,118,346 B2 * | 10/2006 | Read | 416/232 |
| 2002/0017144 A1 * | 2/2002 | Miles et al. | 73/808 |

FOREIGN PATENT DOCUMENTS

| | | |
|---|---|---|
| GB | 2 367 631 A | 4/2002 |
| JP | A 11-173966 | 7/1999 |

* cited by examiner

APPARATUS AND A METHOD FOR TESTING ATTACHMENT FEATURES OF COMPONENTS

The present invention relates to an apparatus and a method for testing attachment features of components and in particular to an apparatus and a method for testing attachment features, e.g. dovetails or firtrees, of compressor blades/discs or turbine blades/discs.

The attachment features of components, e.g. the dovetail roots, or firtree roots, of rotor blades and correspondingly shaped slots in a rotor, suffer from fretting fatigue. This fretting fatigue in the attachment features may lead to the formation of cracking in the attachment features, which limits the useful life of the components, e.g. the rotor blades or rotor discs. Once cracking has started in the attachment features it is necessary to replace the rotor blades or discs.

It is known to test the attachment features of the components by spin testing an actual rotor with attached rotor blades at high speed to evaluate the performance of the attachment features, i.e. to determine the fretting fatigue behaviour of the rotor and rotor blades. The rotor and rotor blades may be operated at speeds simulating and corresponding to those experienced by the rotor in actual use in for example a gas turbine engine and thus simulate the low cycle loading of the rotor blades. However, such spin testing does not simulate the aerodynamic loading, e.g. high cycle loading, of the rotor blades and does not test thermal gradients in the components. In addition the spin testing of a rotor and rotor blades is very expensive and may take several months. Also spin testing is limited because it cannot easily simulate the environment, e.g. oxidation, vibration etc, that the rotor experiences in a gas turbine engine.

Accordingly the present invention seeks to provide a novel apparatus and method for testing attachment features of components.

Accordingly the present invention provides an apparatus for testing attachment features of components comprising a first member having a first end, a second end, a first edge and a second edge, the first edge having a first shaped slot to receive a first component, the first component having an attachment feature correspondingly shaped to fit the first shaped slot, the first end of the first member having flanges extending laterally away from the first member and the second end of the first member having flanges extending laterally away from the first member such that the first member is substantially H-shaped in cross-section, first load means to apply a load on the first component and second load means to apply a load on the first member substantially in the opposite direction to the load on the first component.

Preferably the second edge having a second shaped slot to receive a second component, the second component having an attachment feature correspondingly shaped to fit the second shaped slot, the second load means to apply a load on the second component substantially in the opposite direction to the load on the first component.

Preferably the first loads may be arranged to apply tension and/or torsion loads. Preferably the second load means may be arranged to apply tension and/or torsion loads.

Preferably the flanges at the first end of the first member extend substantially perpendicularly from the first member.

Preferably the flanges at the second end of the first member extend substantially perpendicularly from the first member.

Preferably the first shaped slot in the first edge of the first member is firtree shaped in cross-section. Alternatively the first shaped slot in the first edge of the first member is dovetail shaped in cross-section.

Preferably the second shaped slot in the second edge of the first member is firtree shaped in cross-section. Alternatively the second shaped slot in the second edge of the first member is dovetail shaped in cross-section.

Preferably the first member having support members extending laterally away from the first member, the support members extending between and being secured to the flanges at the first and second ends of the first member, the support members extending between the first and second shaped slots.

Preferably a vibration means is provided to vibrate the first member, the first component and the second component.

Preferably a heating means is provided to heat the first member, the first component and the second component.

Preferably the first component is a compressor blade, a fan blade or a turbine blade. Preferably the second component is a compressor blade, a fan blade or a turbine blade.

Accordingly the present invention provides a method of testing attachment features of components comprising a first member having a first end, a second end, a first edge and a second edge, the first edge having a first shaped slot to receive a first component, the first component having an attachment feature correspondingly shaped to fit the first shaped slot, the first end of the first member having flanges extending laterally away from the first member and the second end of the first member having flanges extending laterally away from the first member such that the first member is substantially H-shaped in cross-section, applying a load on the first component and applying a load on the first member substantially in the opposite direction to the load on the first component.

Preferably the second edge having a second shaped slot to receive a second component, the second component having an attachment feature correspondingly shaped to fit the second shaped slot, and applying a load on the second component substantially in the opposite direction to the load on the first component.

The load applied on the first component may be tension and/or torsion loads. The load applied on the second component may be tension and/or torsion loads.

Preferably the flanges at the first end of the first member extend substantially perpendicularly from the first member.

Preferably the flanges at the second end of the first member extend substantially perpendicularly from the first member.

Preferably the first shaped slot in the first edge of the first member is firtree shaped in cross-section. Alternatively the first shaped slot in the first edge of the first member is dovetail shaped in cross-section.

Preferably the second shaped slot in the second edge of the first member is firtree shaped in cross-section. Alternatively the second shaped slot in the second edge of the first member is dovetail shaped in cross-section.

Preferably the first member having support members extending laterally away from the first member, the support members extending between and being secured to the flanges at the first and second ends of the first member, the support members extending between the first and second shaped slots.

Preferably the method comprises vibrating the first member, the first component and the second component.

Preferably the method comprises heating the first member, the first component and the second component.

Preferably the first component is a compressor blade, a fan blade or a turbine blade. Preferably the second component is a compressor blade, a fan blade or a turbine blade.

The present invention will be more fully described by way of example with reference to the accompanying drawings in which:—

Figure 1:
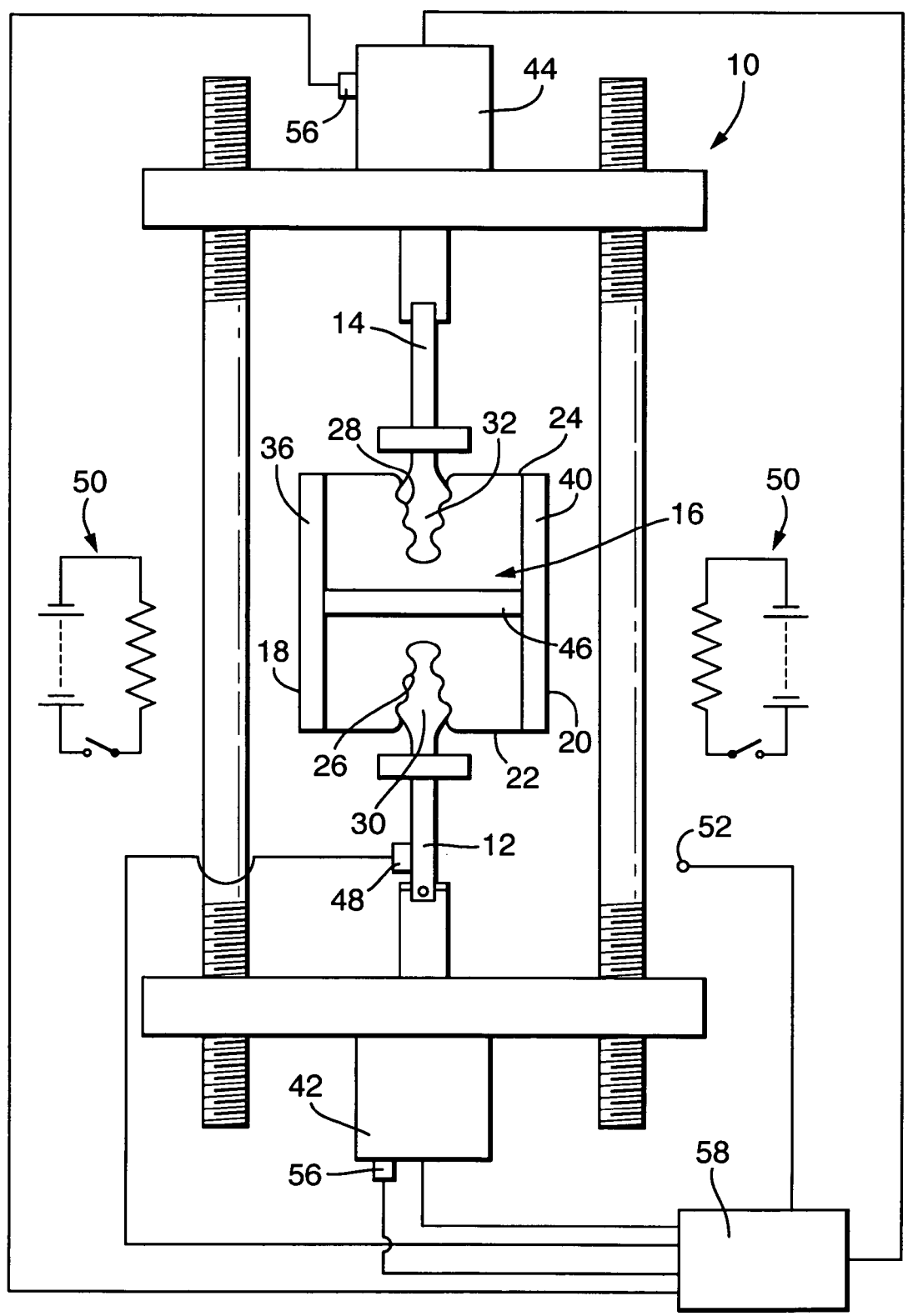
FIG. 1 shows an apparatus for testing attachment features of components according to the present invention.
Figure 2:
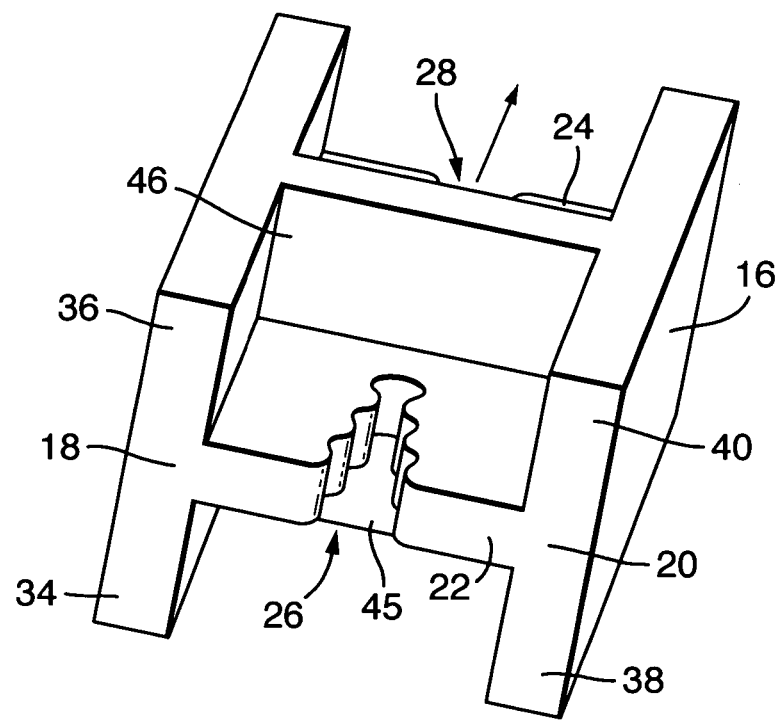
FIG. 2 is a perspective view of a first member for use in the apparatus for testing attachment features of components shown in FIG. 1.

An apparatus 10 for testing attachment features of components 12, 14 is shown in FIGS. 1 and 2. The apparatus 10 comprises a first member 16, which has a first end 18, a second end 20, a first edge 22 and a second edge 24. The first edge 22 has a first shaped slot 26 to receive the first component 12 and the second edge 24 has a second shaped slot 28 to receive the second component 14. The first component 12 has an attachment feature 30 correspondingly shaped to fit the first shaped slot 26 and the second component 14 has an attachment feature 32 correspondingly shaped to fit the second shaped slot 28. The first end 18 of the first member 16 has flanges 34 and 36 extending laterally away from the first member 16 and the second end 20 of the first member 16 has flanges 38 and 40 extending laterally away from the first member 16 such that the first member 16 is substantially H-shaped in cross-section. A first load means 42 is secured to the first component 12 and is arranged to apply a load on the first component 12. A second load means 44 is secured to the second component 14 and is arranged to apply a load on the second component 14 substantially in the opposite direction to the load on the first component 12. Thus the first and second load means 42 and 44 are arranged to apply a tension load on the first and second components 12 and 14 and the first member 16. The first and second load means 42 and 44 may comprise a conventional load cell capable of applying tensile loads of up to several hundred kN, e.g. 200 kN.

It is noted that the flanges 34 and 36 at the first end 18 of the first member 16 extend substantially perpendicularly from the first member 16. Similarly the flanges 38 and 40 at the second end 20 of the first member 16 extend substantially perpendicularly from the first member 16.

The first shaped slot 26 in the first edge 22 of the first member 16 is firtree shaped in cross-section. Thus the attachment feature 30 of the first component 12 is firtree shaped in cross-section. However, the first shaped slot 26 in the first edge 22 of the first member 16 and the attachment feature 30 of the first component 12 may be dovetail shaped in cross-section. The second shaped slot 28 in the second edge 24 of the first member 16 is firtree shaped in cross-section. The attachment feature 32 of the second component 14 is firtree shaped in cross-section. Alternatively the second shaped slot 28 in the second edge 24 of the first member 16 and the attachment feature 32 of the second component 14 may be dovetail shaped in cross-section.

The first member 16 has first and second support members 45 and 46 extending laterally away from the first member 16. The first support member 45 extends between and is secured to the flanges 34 and 38 at the first and second ends 18 and 20 respectively of the first member 16. The second support member 46 extends between and is secured to the flanges 36 and 40 at the first and second ends 18 and 20 respectively of the first member 16. The support members 45 and 46 extend between the first and second shaped slots 26 and 28.

A vibration means 48 is provided to vibrate the first member 16, the first component 12 and the second component 14. The vibration means 48 for example comprises a piezoelectric transducer, a magnetostrictive transducer or mechanical shaker or other suitable device acoustically coupled to the first component 12 and/or the second component 14.

A heating means 50 is provided to heat the first member 16, the first component 12 and the second component 14, if testing is required to be tested at higher temperatures to simulate thermal gradients.

The first component 12 may be a compressor blade, a fan blade or a turbine blade. The second component 14 may be a compressor blade, a fan blade or a turbine blade.

There are temperature sensors 52, displacement sensors 54, force sensors 56 etc to measure temperature, displacement and force and these are stored in processor 58. The temperature, displacement and force sensors are standard sensors. The processor 58 also controls the first load means 42, the second load means 44, the heating means 50 and the vibration means 58.

Figure 3:
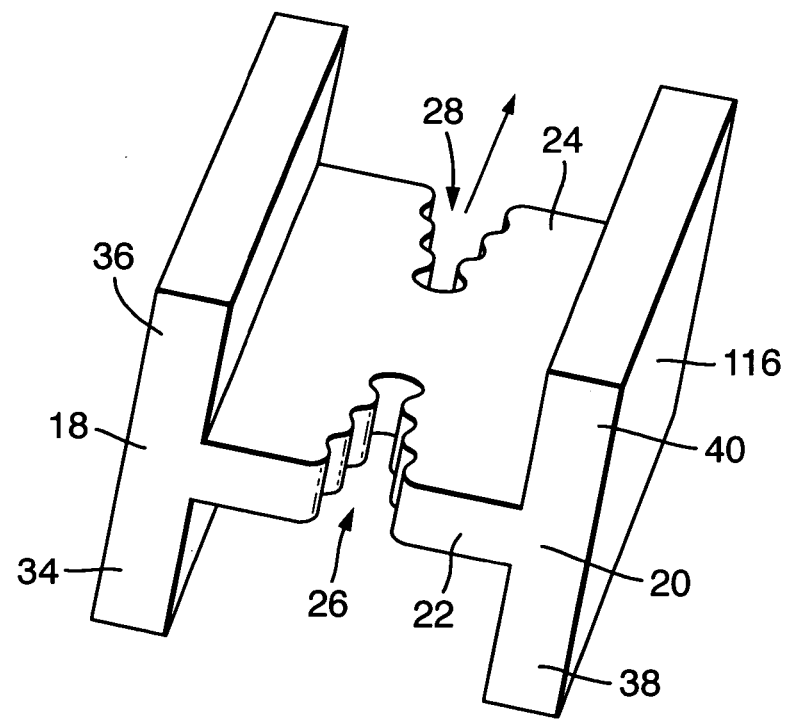
FIG. 3 is a perspective view of an alternative member use in the apparatus for testing attachment features of components shown in FIG. 1.

An alternative first member 116 for testing attachment features of components 12, 14 is shown in FIG. 3. The first member 116 is substantially the same as the first member 16 shown in FIGS. 1 and 2 and like parts are denoted by like numerals. The first member 116 differs in that the first member 116 does not have the supporting members.

Figure 4:
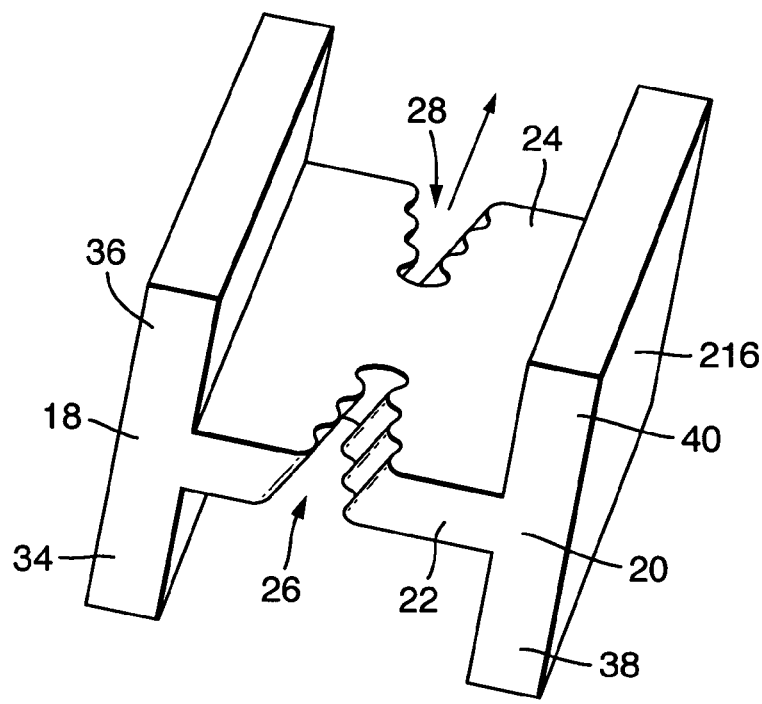
FIG. 4 is a perspective view of a first member for use in the apparatus for testing attachment features of components shown in FIG. 1.

Another first member 216 for testing attachment features of components 12, 14 is shown in FIG. 4. The first member 216 is substantially the same as the first member 16 shown in FIGS. 1 and 2 and like parts are denoted by like numerals. The first member 216 differs in that the first and second shaped slots 26 and 28 in first member 216 are skewed to simulate the skewed slots in a rotor and thus in this arrangement torsion is also applied, which increases the loads at the acute corners of the attachment features to simulate those in the gas turbine engine.

Figure 5:
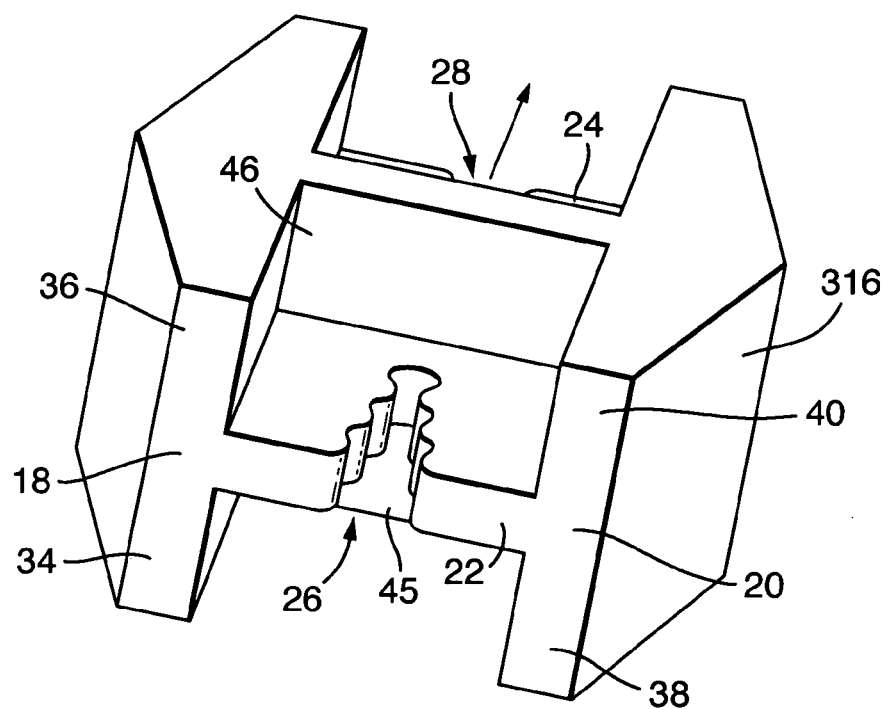
FIG. 5 is a perspective view of an alternative member use in the apparatus for testing attachment features of components shown in FIG. 1.

A further first member 316 for testing attachment features of components 12, 14 is shown in FIG. 5. The first member 316 is substantially the same as the first member 116 shown in FIGS. 1 and 3 and like parts are denoted by like numerals. The first member 316 differs in that the first member 316 has non-uniform shaped flanges 34, 36, 38 and 40 to change the behaviour.

Figure 6:
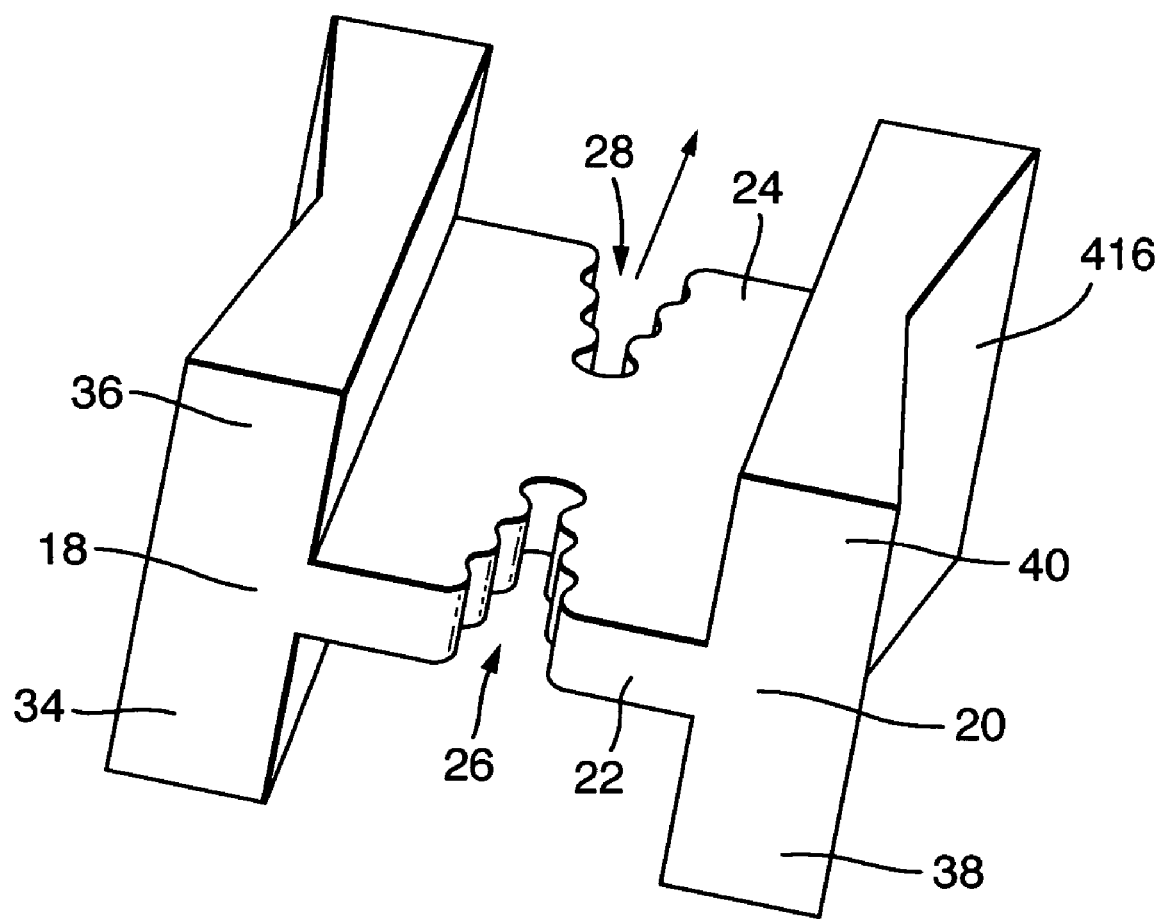
FIG. 6 is a perspective view of a first member for use in the apparatus for testing attachment features of components shown in FIG. 1.

Another first member 416 for testing attachment features of components 12, 14 is shown in FIG. 6. The first member 416 is substantially the same as the first member 116 shown in FIGS. 1 and 2 and like parts are denoted by like numerals. The first member 416 differs in that the first member 416 has non-uniform shaped flanges 34, 36, 38 and 40 to change the behaviour.

Other non-uniform shaped flanges may be used.

In operation the attachment features 30 and 32 of the first and second components, for example compressor rotor blades or turbine rotor blades, 12 and 14 to be tested are placed in the first and second shaped slots, for example firtree shaped slots, 26 and 28 in the first and second edges 22 and 24 respectively of the first member 16. The first and second components 12 and 14 are connected to the first and second load means 42 and 44 respectively and the first and second components 12 and 14 are pulled under tension. The forces applied under normal operation of the first and second components 12 and 14 are applied to the first and second components 12 and 14. These tensile loads open up the first and second slots 26 and 28 by a prescribed displacement, dependent upon the H cross-section first member 16 and the bulk thickness of the first member 16 (or the first and second components 12 and 14). These tensile loads and the movement of the first and second slots 26 and 28 in the first member 16 generate the required crushing stresses on the loading flanks of the first and second slots 26 and 28, the required first component 12 and second component 14 to first member 16 relative displacements, mean section stress (in the locality of the notches in the first and second slots, the firtree slots, 26 and 28, which is important for local contact and notch plasticity in the first and second slots, firtree slots, 26 and 28 and crack propagation) and by careful design do not overload the notch stress levels of the first and second slots, firtree slots, 26 and 28 such that the first member 16 fails in this locality.

The vibration means 48 may be used to vibrate the first member 16 and the first and second components 12 and 14 in the principal force plane to try to replicate the exact conditions experienced by the first and second slots 26 and 28 of the first member 16 and the attachment features 30 and 32 of the first and second components 12 and 14 in an operating environment, e.g. in an operating gas turbine engine environment.

The heating means may be used to heat the first member 16 and the first and second components 12 and 14 to try to replicate the exact conditions experienced by the first and second slots 26 and 28 of the first member 16 and the attachment features 30 and 32 of the first and second components 12 and 14 in an operating environment, e.g. in an operating gas turbine engine environment.

The temperatures, displacements forces etc are measured using standard techniques. These measurements of temperature, displacement and force are used in the processor to produce lifing curves and may be used with engine test data or other test experience to generate design and lifing models for rotor blade and rotor discs or rotor drums for compressors, fans or turbines of gas turbine engines, steam turbines, wind turbines etc.

The first member is essentially monolithic, one piece, design and the first member does not have the disadvantages of complex multiple part tests. The multiple part tests have friction and loading and/or displacement control devices causing inaccuracies in the test and greatly adding to the cost and set up time of the test. The first member does not need lateral clamping or lateral forces to achieve required displacements. Complex loading cycles are not required, only simple tensile loading of the first and second components is required. The H-shaped cross section of the first member reduces, preferably stops, relative first and second components to first member movements exceeding predetermined levels because the H-shaped cross section of the first member provides support against this relative movement, or bending. The H-shaped cross section of the first member may be modified in shape to provide differing relative movements at different notch positions in the first and second slots, of the firtree slots, thus targeting the first member to fail at the ideal failure location and also reduce testing time and cost. The H-shaped cross section first member is additionally supported by the supporting members to further restrain these relative movements.

The first member may be made such that fretting fatigue is the dominant failure mechanism, rather than notch low cycle fatigue (LCF). This is because the first member may be tuned to have differing levels of crushing stress to relative movement, by altering the H-shaped cross section, number of notches/lobes, materials, details of the notch shape(s) etc.

The first member may be used to test different notch/lobe shapes, first and second component designs, different cooling patterns in the first and second components, to replicate real cooled turbine rotor blades, and also contact behaviour by providing coatings between the first and second slots and the attachment features. The coatings may be corrosion resistant coating, wear resistant coatings, lubricant coatings etc.

The first member may also be used to test other attachment features that are subject to fretting fatigue including dovetails, whether they are for stator components or rotor components in a real operating environment.

The first member may also be used to test other attachment features that are subject to fretting fatigue, for example spline couplings, curvic couplings hirth couplings, seals, locking components etc, where forces and relative displacements play a significant part in the fatigue behaviour.

An advantage of the present invention is that the first member is simple, easy to make and is low cost. A further advantage is that it is simple to control, there is no clamping or application of lateral forces and thus it is relatively cheap to provide tests. The H-shaped cross section first member only uses tensile forces in one direction and therefore it may be used in many cheaper less complicated testing devices rather than expensive more complicated testing devices.

An additional advantage is that the device is relatively small and low cost and may be used to test at higher pressures, e.g. up to 30 atmospheres, to simulate oxidation as in a gas turbine engine.

Although the present invention has been described with reference to a first member with first and second shaped slots arranged at it's opposite edges to receive the attachment features of first and second components, it may also be possible to provide a first member with only a first shaped slot in one edge to receive the attachment feature of a first component.

I claim:

1. An apparatus for testing attachment features of components comprising a first member having a first end, a second end, a first edge and a second edge, the first edge having a first shaped slot to receive a first component, the first component having an attachment feature correspondingly shaped to fit the first shaped slot, the first end of the first member having flanges extending laterally away from the first member and the second end of the first member having flanges extending laterally away from the first member such that the first member is H-shaped in cross-section, first load means to apply a load on the first component and second load means to apply a load on the first member substantially in the opposite direction to the load on the first component.

2. An apparatus as claimed in claim 1 wherein the first load means is arranged to apply tension and/or torsion loads.

3. An apparatus as claimed in claim 1 wherein the second load means is arranged to apply tension and/or torsion loads.

4. An apparatus as claimed in claim 1 wherein the flanges at the first end of the first member extend substantially perpendicularly from the first member.

5. An apparatus as claimed in claim 1 wherein the flanges at the second end of the first member extend substantially perpendicularly from the first member.

6. An apparatus as claimed in claim 1 wherein the first shaped slot in the first edge of the first member is firtree shaped in cross-section.

7. An apparatus as claimed in claim 1 wherein the first shaped slot in the first edge of the first member is dovetail shaped in cross-section.

8. An apparatus as claimed in claim 1 wherein the first component is a compressor blade, a fan blade or a turbine blade.

9. An apparatus for testing attachment features of components comprising a first member having a first end, a second end, a first edge and a second edge, the first edge having a first shaped slot to receive a first component, the first component having an attachment feature correspondingly shaped to fit the first shaped slot, the first end of the first member having flanges extending laterally away from the first member and the second end of the first member having flanges extending laterally away from the first member such that the first member is substantially H-shaped in cross-section, first load means to apply a load on the first component and second load means to apply a load on the first member substantially in the opposite direction to the load on the first component,
wherein the second edge having a second shaped slot to receive a second component, the second component having an attachment feature correspondingly shaped to fit the second shaped slot, the second load means to apply a load on the second component substantially in the opposite direction to the load on the first component.

10. An apparatus as claimed in claim 9 wherein the second shaped slot in the second edge of the first member is firtree shaped in cross-section.

11. An apparatus as claimed in claim 9 wherein the second shaped slot in the second edge of the first member is dovetail shaped in cross-section.

12. An apparatus as claimed in claim 9 wherein the first member having support members extending laterally away from the first member, the support members extending between and being secured to the flanges at the first and second ends of the first member, the support members extending between the first and second shaped slots.

13. An apparatus as claimed in claim 9 wherein vibration means is provided to vibrate the first member, the first component and the second component.

14. An apparatus as claimed in claim 9 wherein heating means is provided to heat the first member, the first component and the second component.

15. An apparatus as claimed in claim 9 wherein the second component is a compressor blade, a fan blade or a turbine blade.

16. A method of testing attachment features of a component, the method comprising:
placing on a test apparatus, a component having a first member having a first end, a second end, a first edge and a second edge, the first edge having a first shaped slot to receive a first component, the first component having an attachment feature correspondingly shaped to fit the first shaped slot, the first end of the first member having flanges extending laterally away from the first member and the second end of the first member having flanges extending laterally away from the first member such that the first member is H-shaped in cross-section, and
applying a load on the first component and applying a load on the first member substantially in the opposite direction to the load on the first component.

17. A method as claimed in claim 16 wherein the load on the first component is a tension and/or torsion load.

18. A method as claimed in claim 16 wherein the flanges at the first end of the first member extend substantially perpendicularly from the first member.

19. A method as claimed in claim 16 wherein the flanges at the second end of the first member extend substantially perpendicularly from the first member.

20. A method as claimed in claim 16 wherein the first shaped slot in the first edge of the first member is firtree shaped in cross-section.

21. A method as claimed in claim 16 wherein the first shaped slot in the first edge of the first member is dovetail shaped in cross-section.

22. A method of testing attachment features of components comprising a first member having a first end, a second end, a first edge and a second edge, the first edge having a first shaped slot to receive a first component, the first component having an attachment feature correspondingly shaped to fit the first shaped slot, the first end of the first member having flanges extending laterally away from the first member and the second end of the first member having flanges extending laterally away from the first member such that the first member is substantially H-shaped in cross-section,
wherein the second edge having a second shaped slot to receive a second component, the second component having an attachment feature correspondingly shaped to fit the second shaped slot, and
the method comprising applying a load on the first component and applying a load on the first member substantially in the opposite direction to the load on the first component, and applying a load on the second component substantially in the opposite direction to the load on the first component.

23. A method as claimed in claim 22 wherein the load on the second component is a tension and/or torsion load.

24. A method as claimed in claim 22 wherein the second shaped slot in the second edge of the first member is firtree shaped in cross-section.

25. A method as claimed in claim 22 wherein the second shaped slot in the second edge of the first member is dovetail shaped in cross-section.

26. A method as claimed in claim 22 wherein the first member having support members extending laterally away from the first member, the support members extending between and being secured to the flanges at the first and second ends of the first member, the support members extending between the first and second shaped slots.

27. A method as claimed in claim 22 comprising vibrating the first member, the first component and the second component.

28. A method as claimed in claim 22 comprising heating the first member, the first component and the second component.

29. A method as claimed in claim 22 wherein the first component is a compressor blade, a fan blade or a turbine blade.

30. A method as claimed in claim 22 wherein the first component is a compressor blade, a fan blade or a turbine blade.

* * * * *